US008827986B2

(12) United States Patent
Shachar et al.

(10) Patent No.: US 8,827,986 B2
(45) Date of Patent: Sep. 9, 2014

(54) REMOTELY ACTIVATED PIEZOELECTRIC PUMP FOR DELIVERY OF BIOLOGICAL AGENTS TO THE INTERVERTEBRAL DISC AND SPINE

(75) Inventors: Yehoshua Shachar, Santa Monica, CA (US); Thomas C. Chen, La Canada, CA (US); Leslie Farkas, Ojai, CA (US); Brett Jordan, Los Angeles, CA (US); Kyle Zimmerman, Los Angeles, CA (US); Herwin Chan, Los Angeles, CA (US); Winston Wu, Alhambra, CA (US)

(73) Assignee: Pharmaco-Kinesis Corporation, Los Angeles, CA (US)

( * ) Notice: Subject to any disclaimer, the term of this patent is extended or adjusted under 35 U.S.C. 154(b) by 772 days.

(21) Appl. No.: 12/581,785

(22) Filed: Oct. 19, 2009

(65) Prior Publication Data
US 2011/0092948 A1   Apr. 21, 2011

(51) Int. Cl.
*A61K 9/22*   (2006.01)
*A61F 2/44*   (2006.01)
*A61M 5/142*   (2006.01)
*A61M 5/145*   (2006.01)
*A61M 37/00*   (2006.01)
*A61F 2/30*   (2006.01)
*A61F 2/28*   (2006.01)

(52) U.S. Cl.
CPC ........ *A61M 37/00* (2013.01); *A61F 2002/3067* (2013.01); *A61F 2002/30787* (2013.01); *A61M 2205/0294* (2013.01); *A61F 2/4465* (2013.01); *A61M 5/14276* (2013.01); *A61F 2002/30785* (2013.01); *A61F 2002/30841* (2013.01); *A61F 2002/3092* (2013.01); *A61F 2310/00023* (2013.01); *A61M 5/1452* (2013.01); *A61F 2002/2817* (2013.01); *A61M 2205/8243* (2013.01); *A61F 2002/4475* (2013.01); *A61F 2002/30677* (2013.01); *A61M 2210/1003* (2013.01)
USPC .................... 604/891.1; 604/151; 604/500

(58) Field of Classification Search
USPC .................... 604/151, 288.04, 500, 891.1
See application file for complete search history.

(56) References Cited

U.S. PATENT DOCUMENTS

| 4,944,659 | A | * | 7/1990 | Labbe et al. ............... 417/413.2 |
| 5,549,679 | A | * | 8/1996 | Kuslich ....................... 623/17.12 |
| 6,315,769 | B1 | * | 11/2001 | Peer et al. ................... 604/891.1 |
| 2006/0224140 | A1 | * | 10/2006 | Junker ........................... 604/502 |
| 2007/0250045 | A1 | * | 10/2007 | Trieu ........................... 604/890.1 |
| 2008/0025987 | A1 | * | 1/2008 | Beals et al. ................. 424/145.1 |
| 2010/0191088 | A1 | * | 7/2010 | Anderson et al. ............. 600/373 |
| 2010/0222750 | A1 | * | 9/2010 | Cheng ........................ 604/288.04 |
| 2010/0256710 | A1 | * | 10/2010 | Dinsmoor et al. .............. 607/61 |
| 2011/0046697 | A1 | * | 2/2011 | Gerber et al. .................... 607/59 |

* cited by examiner

*Primary Examiner* — Emily Schmidt
(74) *Attorney, Agent, or Firm* — Marcus C. Dawes; Daniel L. Dawes

(57) ABSTRACT

A remotely activated piezoelectric pump for delivery of biological agents to the intervertebral disc and spine in order to achieve spinal fusion. A spinal pump is implanted on the vertebrae of a patient and a spinal cage is inserted in between two adjacent vertebrae after removal of the vertebrae disc. A piezoelectric motor drives the pump and pushes osteogenetic agent through the spinal cage and into a sponge disposed within the cage. The pump is charged by an external removable induction belt worn by the patient. Delivery duration and delivery frequency may be changed before implantation of the spine pump according to the specific needs of the patient. The current device employs a mathematical model that enables the regulation as well as attenuation of the bone fusion process by extending and generalizing the model to enhance and optimize the delivery of osteogenetic agent in a regulated manner.

6 Claims, 13 Drawing Sheets

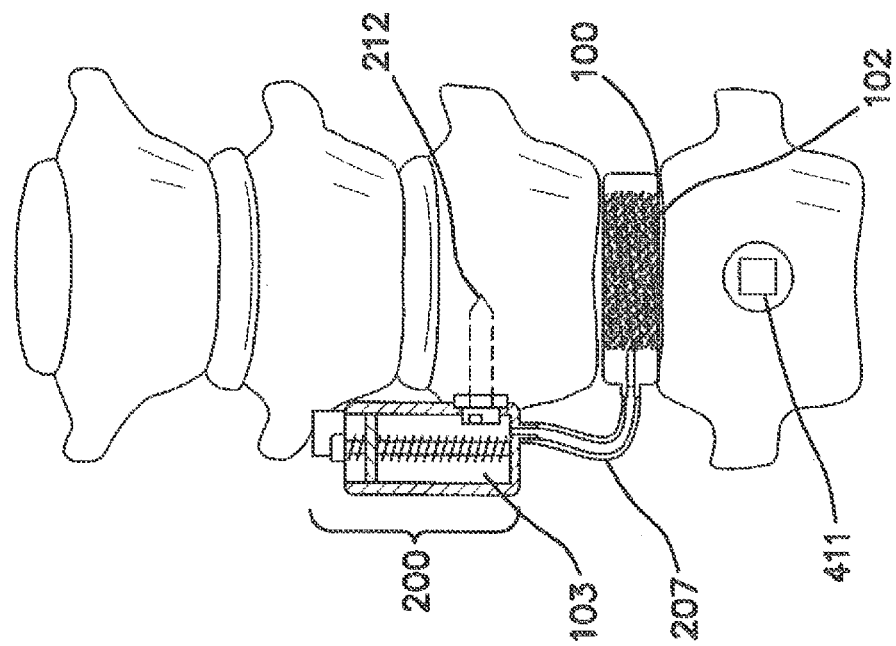
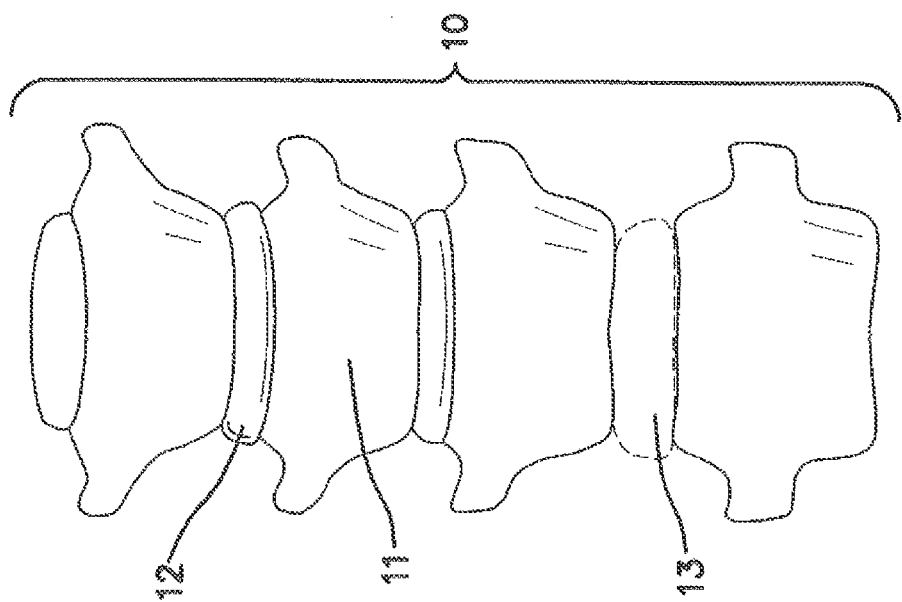

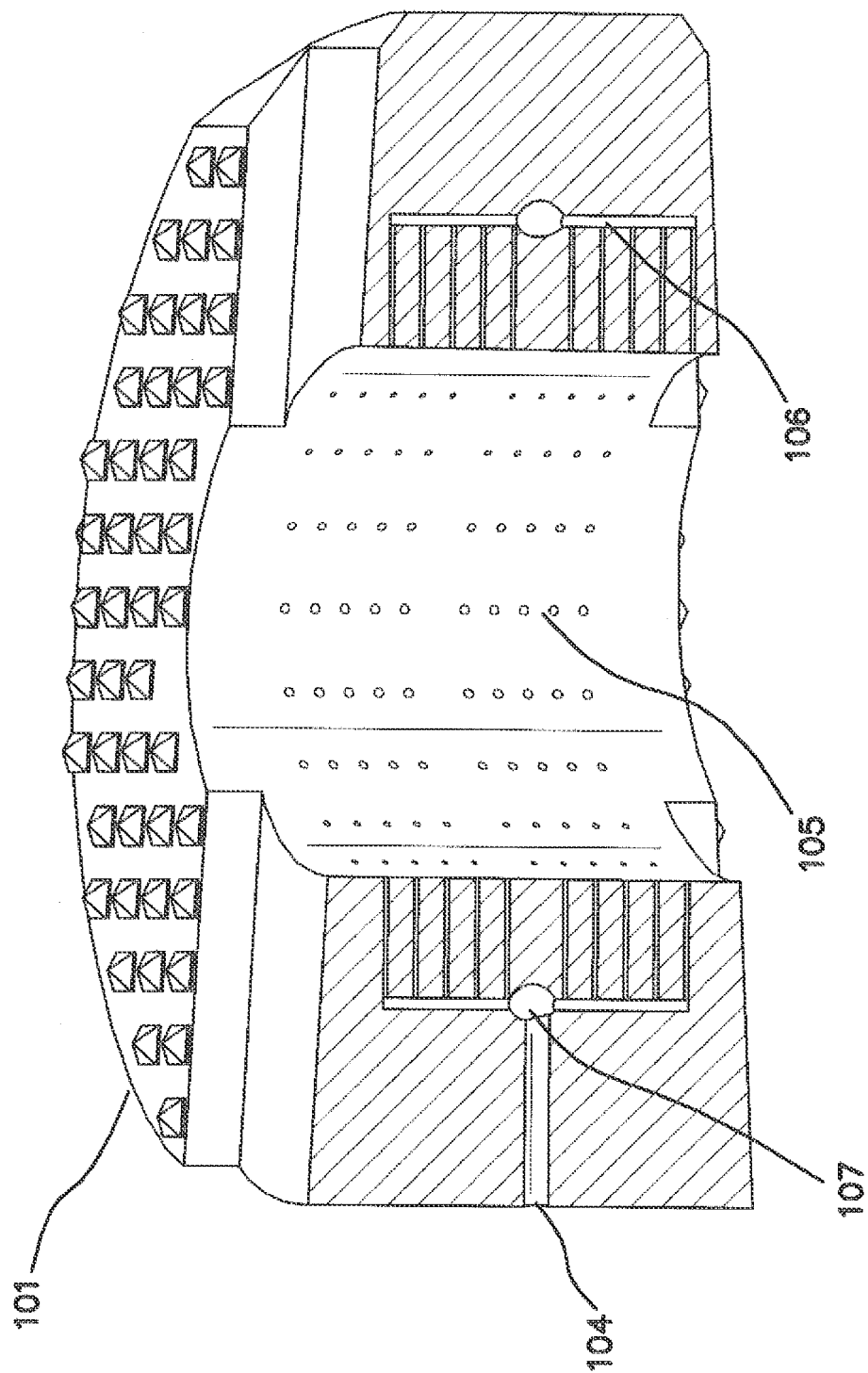

REMOTELY ACTIVATED PIEZOELECTRIC PUMP FOR DELIVERY OF BIOLOGICAL AGENTS TO THE INTERVERTEBRAL DISC AND SPINE

BACKGROUND OF THE INVENTION

1. Field of the Invention

The invention relates to the field of implantable drug delivery systems, specifically to a remotely activated piezoelectric pump for the controlled delivery of biological agents to the disc space and spine.

2. Description of the Prior Art

Scientists and spinal surgeons have demonstrated that a genetically produced protein, recombinant human bone morphogenetic protein-2, or rhBMP-2, has the ability to stimulate a patient's own cells to make more bone. This finding has obvious beneficial implications for the treatment of many bone fractures and bone defects. More importantly, though, rhBMP-2 can be tremendously beneficial to patients undergoing spinal fusion. RhBMP-2 will eliminate the need for bone transplantation from the pelvis. It may also more reliably and more quickly produce fusion of spinal vertebrae. It may even reduce the need for the implantation of spinal rods and screws.

Back pain is one of the 15 most commonly treated medical conditions in the United States today and is second only to the common cold as the most common reason for physician visits. Back pain not only has a profound effect on patients, it has an exceedingly high societal cost. Back pain is the second most common cause of lost productive time of the pain disorders and results in the largest amount of total lost time. It has been stated that of all medical conditions, back pain results in the most lost productivity. It is estimated that the direct and indirect costs associated with the disorder are approximately 50 billion dollars per year in the United States alone. Although back pain is multifactorial, degenerative disc disease is often involved in the pathogenesis and subsequent propagation of lower back pain. The disc space is composed of disc and surrounding annulus fibrosus. As the disc degenerates hypertrophy is increased in order to support the body weight, eventually leading to back pain.

The achievement of a bony fusion is necessary for bony regeneration and healing, and is crucial to the success of many orthopedic procedures. In the spine alone, it is estimated that more than 300,000 spinal fusion procedures are performed each year in the United States.

Traditionally, spinal fusions have been performed by decorticating the host bone, and laying down autograft from the iliac crest to achieve a bony "in-situ" fusion. With the advent and popularity of instrumentation for spinal fusions (i.e. pedicle screws), adjacent segments could now be held together, immobilizing them, thus enhancing the fusion rate. However, even with the use of iliac crest autograft and spinal fixation, the development of a biologic fusion—i.e., new bone formation at the fusion site, is not consistent. Spinal fixation allows for short term mechanical stabilization, but lacks the capacity to produce a consistent biologic fusion. Iliac crest autografts have associated morbidities related to the harvesting, including pain at the donor site. Moreover, the consistency of the bone harvested is dependent on patient's intrinsic bone quality and the surgeon's ability to harvest a significant amount of bone needed for a bony fusion. The need for a bone graft substitute that can consistently lead to bony fusions without the need for iliac crest autografts has resulted in the production of bone graft substitutes, such as demineralized bone matrix (DBM). DBM is a bone graft extender, made of allograft, which has the capacity to be osteoconductive, that is, serve as a bridge between two bone chips to facilitate a fusion. DBM, however, is not capable of forming new bone (osteoinductive).

The commercialization of recombinant human bone morphogenetic protein-2 (BMP-2) has lead to a product that has osteoinductive properties that may be used to consistently produce a bony fusion. Currently, BMP-2 is FDA approved as a replacement for autograft in anterior lumbar interbody fusion (ALIF) using an anterior cage. It is marketed as INFUSE Bone Graft by Medtronics, Inc. INFUSE is made up of recombinant BMP-2 and absorbable collagen sponge (ACS; from bovine Achilles tendon). In a typical operation, BMP-2 is added to the ACS for a minimum of 15 minutes prior to implantation to ensure adequate binding of BMP-2. Once added to ACS, the BMP-2 must be used within 2 hours. The mean residence time of BMP-2 after implantation has been measured in a rat femoral onlay model implantation model to be 7.8 days. The maximum level of BMP-2 detected in the circulation was 0.1% of the implanted dose after six hours. In a rat long bone ectopic implant model, the mean residence time ranged from 3.6 to 4.6 days (McKay—p. 72). In human patients, BMP-2 is estimated to be present at the implant site for 3-4 weeks, and is cleared from the blood by the liver and excreted via the urine. Histology from animal models suggests that the ACS is reabsorbed in 4-12 weeks.

Although BMP-2 is only FDA approved for anterior lumbar fusions, it has already been used in many different types of spinal fusion surgeries, including posterolateral fusions, and anterior cervical fusions. The posterolateral fusions appear to be effective with BMP-2 (although there was concern that it may actually work too well, and cause spinal stenosis). The anterior cervical fusions were effective from the standpoint of cervical fusions, but often induced tracheal-esophageal swelling, leading to emergency intubations in some patients. BMP-2 for human bones is used at the concentration of 1.5 mg BMP-2 per 1 cc of solution. In a typical anterior lumbar fusion, the cage is filled with 4 cc of collagen sponge, saturated with 4 cc of the 1.5 mg/cc BMP-2 solution.

The current limitations of the BMP-2 technology are as follows:

i) BMP-2 is soaked into a collagen sponge. When the sponge is implanted, any squeezing or manipulation of the sponge results in loss of BMP-2, making the delivery technique inefficient. ii) BMP-2 half-life and time in circulation is short, usually less than a week, and an average fusion takes 3-6 months to complete. iii) Current BMP-2 has to be delivered at massive quantities compared to what is actually needed (milligram doses, as opposed to nanogram or microgram doses of what is needed), costing health insurance and consumers up to $8,000 to $10,000 per implant. Moreover, increased amounts of BMP-2 placed in the cervical or lumbar spine can lead to a tremendous amount of swelling. iv) BMP-2 delivery is not well directed, and is only passively absorbed. As a result, BMP-2 placed posterolaterally has the potential of fusing too much, leading to spinal stenosis. BMP-2 placed in the anterior cervical spine leads to swelling, from the BMP-2 passively leaking into the adjacent soft tissue. v) Fusion is established purely via a radiographic impression of bone formation via x-rays or CT-scan. No physiological monitoring of motion is placed to establish that a fusion has been established.

The infusion of growth factors to the intervertebral disc has been explored by various authors in the prior art. All the infusions, however, have been via direct one time infusions, or in experimental models via an external catheter.

What is needed is a method and apparatus that provides continuous infusion of various growth factors into the disc space to preserve it, instead of removing and fusing it in order to alleviate the thousands of patients currently suffering from chronic low back pain.

BRIEF SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole. Additional objects and advantages of the current invention will become apparent to one of ordinary skill in the art upon reading the specification.

The invention described herein is directed specifically to the infusion of biological agents to the spine and disc space. Although the concept of delivery of biological agents is similar, different devices will be tailor made for delivery depending on location of placement (i.e. posterior versus anterior spinal column, or intervertebral disc). Moreover, the biological agent to be used will be different, depending on the disease process to be treated. For instance, in the degenerating disc, it may be used for the direct infusion of biological growth factors to preserve degenerating discs. In the case where the interbody disc is removed during surgery, it may be placed into an interbody graft to slowly release bMP-2 placed for an interbody fusion. It may also be placed for posterolateral fusion.

The present disclosure also describes an apparatus that allows an architecture for constructing a remotely activated piezoelectric pump for delivery of biological agents to the intervertebral disc and spine. Furthermore, the current device provides the physician with a parametric bone development model relative to a parametric delivery of dose, duration and structural adhesion of the bone formation as a measure of BMP-2 infusion as characterized by differentiation and growth of chondrocytes from the proliferation zone to the hypertrophying one. These two cellular processes are controlled by a complex signaling regulatory loop between different biochemical signals, whose production depends on the current cell density, constituting a coupled cell-chemical system. The current invention employs a mathematical model that enables the regulation as well as attenuation of the process by extending and generalizing the model to enhance and optimize the delivery of BMP-2 in a regulated manner. A reaction-diffusion regulatory loop between the medicating agents and the disc space is measured by the use of a predictable algorithm. The model represented as a set of equations is further solved within a finite element framework, getting an estimation of the spatial distribution, growth of the bone structure and formation. The results obtained are assumed to be qualitatively similar to the actual physiological ones and quantitatively close to some available experimental data noted by clinical studies.

An object of the current invention is to provide a patient with a metronomic infusion of BMP-2 over the course of a fusion. The piezoelectric pump currently proposed will be able to deliver biological agents such as BMP-2 in a controlled fashion, allowing a more sustained infusion of BMP-2 of up to 3 months.

Fusions will be divided into interbody anterior fusions and posterolateral fusions. For anterior interbody fusions, a bony femoral allograft, PEEK cage, titanium cage, or titanium expandable cage is used in ALIFs or in anterior spine surgery. For posterolateral fusions, the pump will be coupled to a irrigating catheter so that it can be placed in the posterolateral gutter to deliver BMP-2 over the bony fusion.

Another object of the current invention is to store the BMP-2 in an implant reservoir, which may be accessed externally and refilled multiple times with the use of a syringe. The BMP-2 content in the reservoir is then delivered into the spine disc via a small pump.

It is further an object of the invention to employ a micro piezoelectric actuator such as a squiggle motor, which is a type of extremely small ultrasonic piezo linear motor suitable for use in highly miniaturized devices. These simple, robust piezo motors can be scaled down to much smaller sizes than electromagnetic motors without significant loss of power efficiency, which makes them ideal for this implant application.

Furthermore, is an additional object of the invention to enclose the piezoelectric pump so that it is protected in a PEEK or titanium housing that is capable of withstanding impacts and changes in pressure within the spinal column due to body motion. The titanium housing is designed to fit the specific indication and anatomy of the spine in which it will be implanted.

In another embodiment, the invention comprises a pump whose actuation can be energized and controlled from an inductive power source. The pump and its electronics will remain passive until power is received from the control units via inductive coils. The control unit communicates to the implant over the inductive link for on/off control of the pump and to adjust the rate of infusion of the BMP-2. When energized and control signals are received from the inductive coupling, the pump releases BMP-2 into a delivery catheter at the commanded rate, allowing the control unit to adjust the rate of infusion of BMP-2. In addition, the inductive power energizes a plurality of mechanosensors whose values can be queried via the said inductive communication link.

Another object of the invention is to direct intradiscal delivery of BMP-2 via a delivery catheter to irrigation channels in the interbody cage so that it is not just absorbed in a passive manner, but is directed and irrigating the specific fusion site. The irrigation channels are shaped and configured so that BMP-2 is delivered equally throughout the interbody cage.

In another embodiment of the invention, two mechanosensors are placed, one within the pumping unit and a second on the adjacent vertebra. The mechanosensors provide information on how the fusion is progressing on a mechanical basis by physiological monitoring of relative motion between the two vertebras above and below the fusion disc. The data on the progress of the fusion between the two spinal bone segments, which is sent via the inductive communication link, helps a physician monitor the progress of the fusion and ascertain whether an optimal fusion has taken place. When the two bone segments are totally fused, the difference in acceleration of the two vertebras should be become negligible.

It is yet another object of the invention is to provide the concept of restoration. Instead of removing and fusing a disc space as is done in the prior art, the current invention provides a constant infusion of biological agents into the disc space to preserve its integrity and to repair a disc that is damaged from degenerative disease. The infusion is performed by an implanted pump which is capable of being refilled subcutaneously via an external needle, allowing for varying concentrations and types of growth factors to be infused directly into the disc space.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 2a is a frontal lumbar view of the spinal column of a patient before placement of the spinal pump and interbody spinal cage.

FIG. 2b is a frontal lumbar view of the spinal column of a patient after placement of the spinal pump and interbody spinal cage.

FIG. 3b is a magnified plan view of the spinal pump assembly shown in FIG. 3a.

FIG. 5b is an isometric vertical cross section of the interbody spinal cage showing the internal system of channels that connect the inlet port to the outlet pores.

FIG. 8 is an orthographic view of the inductive charger in a belt.

Figure 1:
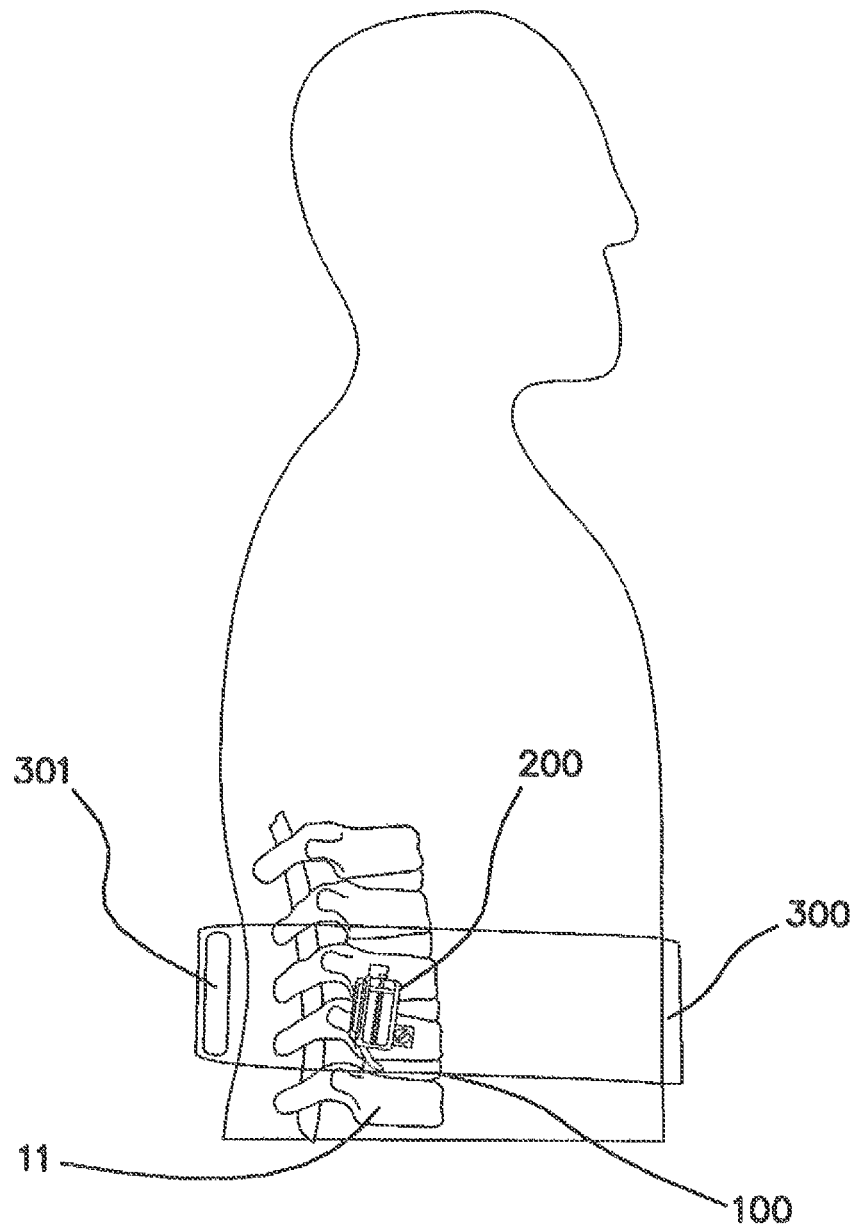
FIG. 1 is a lateral cross sectional view of the spinal pump in its relation to the spine of a patient.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DEFINITIONS

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the methods, devices, and materials are now described. All publications mentioned herein are incorporated herein by reference for the purpose of describing and disclosing the materials and methodologies which are reported in the publications which might be used in connection with the invention. Nothing herein is to be construed as an admission that the invention is not entitled to antedate such disclosure by virtue of prior invention.

"Absorbable Collagen Sponge" as used herein refers to the sponge in the center of the carrier matrix designed to eventually be broken down and absorbed by the body as bone grows through it. It is made up of collagen which is the main protein of connective tissue in animals and the most abundant protein in mammals. Collagen has great tensile strength, and is the main component of fascia, cartilage, ligaments, tendons, bone and skin.

"Anterior lumbar fusion" as used herein refers to an operation done on the front (the anterior region) of the lower spine. Fusion surgery helps two or more bones grow together into one solid bone. Fusion cages are new devices, essentially hollow screws filled with bone graft, that help the bones of the spine heal together firmly. Surgeons use this procedure when patients have symptoms from disc degeneration, disc herniation, or spinal instability.

"Anterior Lumbar Interbody Fusion Device" as used herein refers to the allograft spacers similar to those produced by Synthes North America to meet the specific demands of spinal applications. "Bone Morphogenetic Proteins (BMP)" as used herein refers to a group of growth factors and cytokines known for their ability to induce the formation of bone and cartilage.

"Carrier Matrix" as used herein refers to biomaterials for the orthopedic implant market which, when placed in a bone defect, provide scaffolding through and around which the patient's new bone will grow, gradually replacing the carrier matrix as the target site heals.

"Comprising" as used herein refers to including, but not limited to, whatever follows the word "comprising". Thus, use of the term "comprising" indicates that the listed elements are required or mandatory, but that other elements are optional and may or may not be present. Additionally, unless otherwise noted, exemplary lists of compounds or devices should not be construed as limiting; instead, it should be understood that such lists admit to additional, suitable items not explicitly indicated.

"Controlled Administration System" as used herein refers to a system which provides localized delivery either continuously or intermittently.

"Inductive Power" as used herein refers to powering electronics using electromagnetic induction. A supplying induction coil sends energy through inductive coupling to a receiving inductive coil in an electrical device, which utilizes the energy. Because there is a small gap between the two coils, inductive charging is one kind of short-distance wireless energy transfer.

"Interbody spinal cages" are rigid (i.e. titanium, PEEK, or allograft) spacers, usually cylindrical, that are placed in the disc space. The cages are porous and allow the bone graft to grow from the vertebral body through the cage and into the next vertebral body.

"Localized Delivery" as used herein refers to non-systemic delivery to a site within approximately 10 cm of the site where bone growth is desired.

"Osteogenic" as used herein refers to the ability to generate or stimulate bone growth.

"Osteoconduction" as used herein refers to the ability to stimulate the attachment, migration, and distribution of vascular and osteogenic cells within the carrier matrix material.

"Piezoelectric" as used herein refers to the ability of some materials to generate an electric field or electric potential in response to applied mechanical stress. The piezoelectric effect is reversible in that materials exhibiting the direct piezoelectric effect (the production of an electric potential when stress is applied) also exhibit the reverse piezoelectric effect (the production of stress and/or strain when an electric field is applied).

"PEEK", or Polyether-etherketone, is a hard radiolucent plastic that is used in conjunction with carbon fiber reinforcement or as pure PEEK. Most manufacturers who use PEEK use radio marker dots so the surgeon can see where the implant meets the vertebral body endplate. Numerous companies (Zimmer Spine, Surgicraft, SCIENT'X, and Depuy Spine) have all developed lines of interbody fusion devices using PEEK technology.

The following mathematical symbols used herein refer to its definitions as follow: Q is infusate flow rate; $\rho$ is fluid density; $\vec{v}_f$ is fluid velocity vector in the catheter; $\mu$ is fluid viscosity; $\epsilon$ is tissue porosity; p is infusion fluid pressure; $\vec{\nabla}p$ is pressure gradient; $D_b$ is bulk diffusivity; $D_e$ is effective diffusion tensor; $C_f$=Concentration of drug; $\vec{v}_t$ is fluid velocity in the porous tissue; $D_e$ is mean effective diffusivity; k is first order rate constant accounting for drug reaction; $\Re$ is Hydraulic conductivity tensor, which is a function of fluid viscosity $\mu$ and effective tissue permeability tensor $\kappa$; $\vec{v}_t \cdot \vec{\nabla} C_t$ is convection term; $D_e \vec{\nabla} C_t$ is diffusion flux; $C_f(\vec{x},t)$ is tissue averaged species concentration; $R(C_f, \vec{x})$ is drug decomposition due to metabolic reaction; and $S(C_f, \vec{x})$ is sink term due to bio-elimination.

DETAILED DESCRIPTION OF THE PREFERRED EMBODIMENTS

FIG. 1 is a lateral cross sectional view of the disclosed spinal implant system in its relation to the spine of a patient. The system is intended for lumbar spinal vertebrae 11 located in the low back side of the human body. The spinal implant system comprises an implanted spinal pump 200 which delivers biological agents such as BMP-2 to an interbody spinal cage 100 that is substantially doughnut shaped. The spinal implant system also comprises an external induction unit 300 that charges and controls the spinal pump 200 and via an inductive link. The induction unit 300 comprises an inductive charger and control unit 301.

Figure 2D:
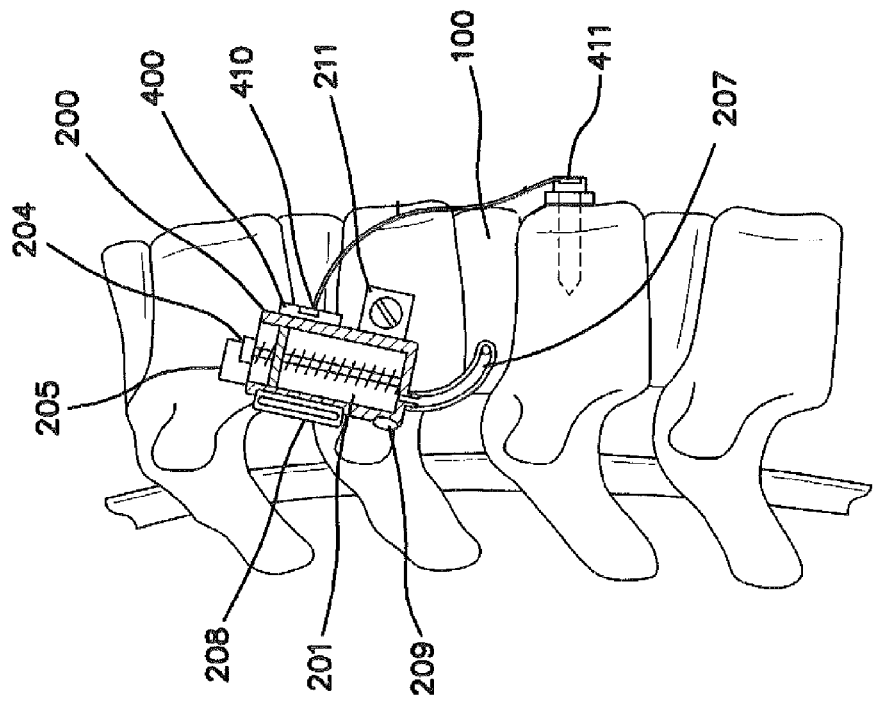
FIG. 2d is a side lumbar view of the spinal column of a patient after placement of the spinal pump and interbody spinal cage.
Figure 2C:
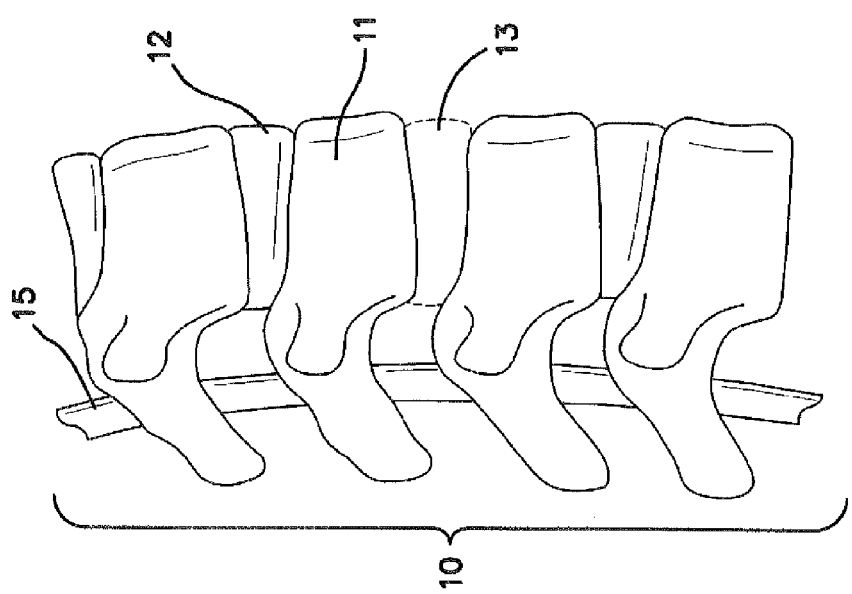
FIG. 2c is a side lumbar view of the spinal column of a patient before placement of the spinal pump and interbody spinal cage.

FIGS. 2a and 2c show the front (anterior) and lateral side view respectively of the lumbar spine 10, spinal nerve 15, and normal vertebrae discs 12 before the replacement of an interbody disc 13 with the interbody spinal cage 100. FIGS. 2b and 2d show the anterior and lateral side view respectively of the lumbar spine 10, spinal nerve 15, and normal vertebrae discs 12 after the replacement of the interbody disc 13 with the interbody spinal cage 100. The system configuration includes the implantable pump 200 coupled to both the adjacent lumbar spinal vertebrae 11 and the interbody cage 100. The interbody spinal cage 100 is specifically configured to work with the implantable spinal pump 200. The interbody spinal cage 100 is placed in between two adjacent vertebrae 11 into the space where the interbody disc 13 previously occupied.

The implantable spinal pump 200 is then securely mounted to the adjacent vertebra 11 via a bracket 211 and a fastening screw 212. The spinal pump 200 is coupled to the interbody spinal cage 100 via a catheter 207. A piezoelectric motor or linear actuator 205 disposed on top of the spinal pump 200 controls the release of the biological agents 103 such as BMP-2 from a reservoir 201 within the spinal pump 200. The spinal pump 200 is powered and controlled wirelessly by an external belt unit 300 seen in FIG. 1 via a plurality of pump inductive coils 208. Additionally, two accelerometers 410, 411 may be coupled to the system in order to monitor the progress of the fusion process by detecting relative motion between the two adjacent vertebrae 11.

Figure 3A:
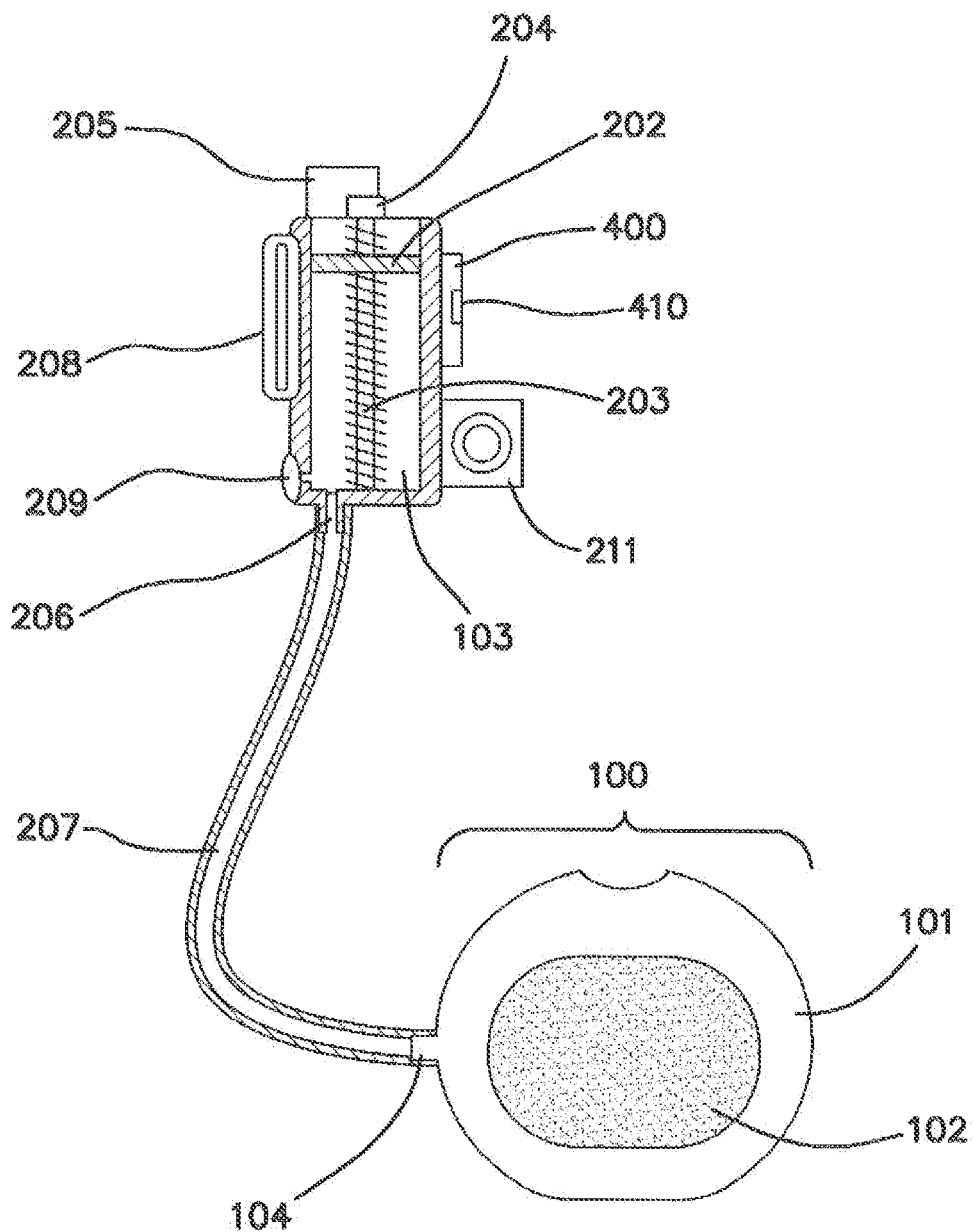
FIG. 3a is a frontal plan view of the spinal pump and interbody spinal cage and their respective components.
Figure 3B:
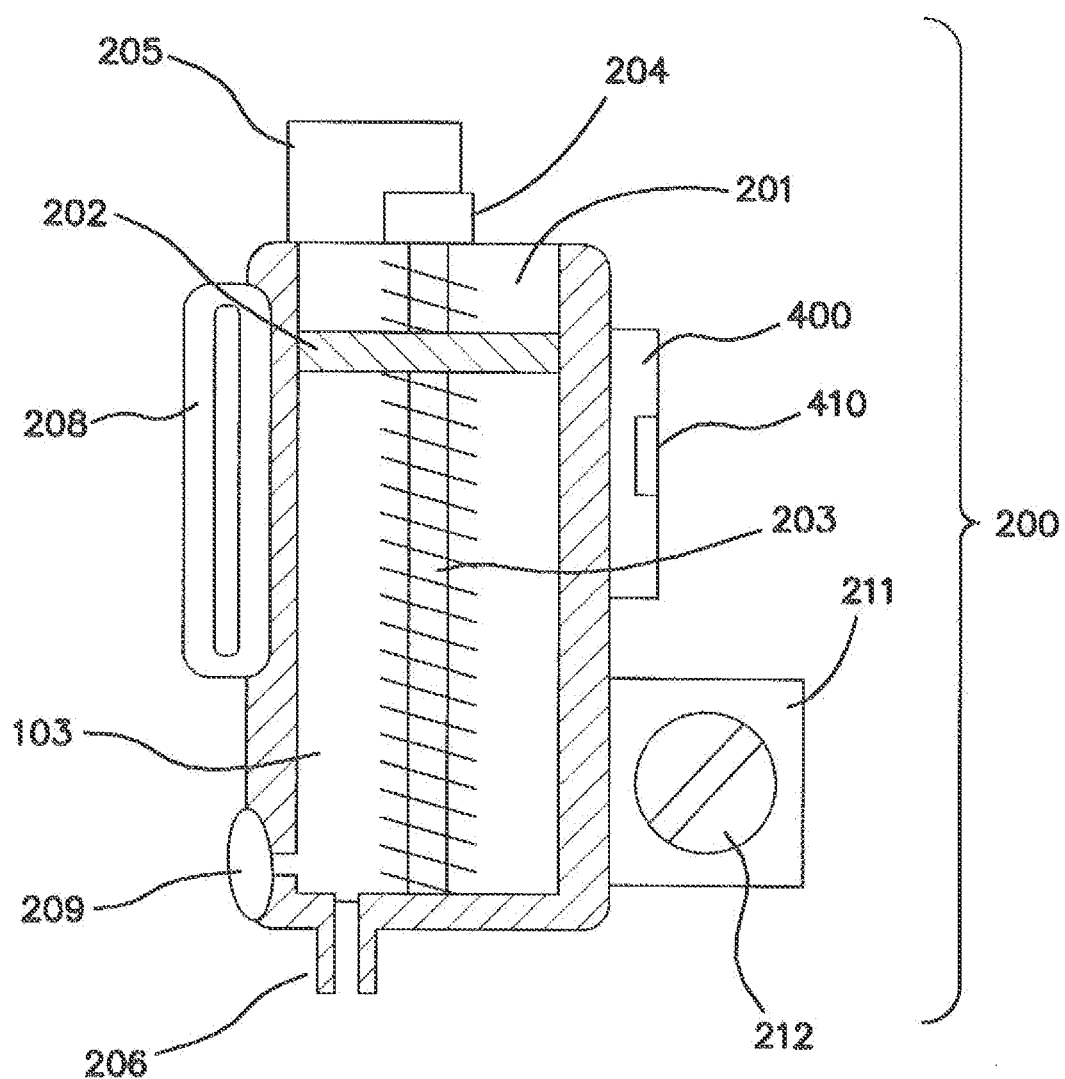

Turning now to FIGS. 3a and 3b which provides a more detailed depiction of the spinal pump 200 and the interbody cage 100, the various detailed components of the pumping system can now be seen. The spinal pump 200 is a standard piston-style pump known in the art in which the osteogenetic agent 103 such as BMP is stored in a reservoir 201. The osteogenetic agent 103 is propelled out of an outlet port 206 by means of a plunger 202. Plunger motion is provided by a worm gear 203 which is actuated by the piezoelectric motor or linear actuator 205. The osteogenetic agent 103 is pushed out of the reservoir 201 when the motor 205 and a pump electrical control system 400 are energized by the pump inductive coils 208. The reservoir 201 is refilled by driving the worm gear 203 backwards while accessing the reservoir 201 with a syringe needle (not shown) via a self-sealing refill port 209.

The piezoelectric motor or linear actuator 205 is an actuator such as a squiggle motor known in the art as an extremely small ultrasonic piezoelectric linear motor suitable for use in highly miniaturized devices. These simple, robust piezoelectric motors can be scaled down to much smaller sizes than electromagnetic motors without significant loss of power efficiency which makes them ideal for the current application. A squiggle motor consists of several piezoelectric ceramic actuators (not shown) coupled to a threaded nut and a pinion 204 with the mating of the worm gear 203 inside. The rotating nut turns the worm gear 203, creating a smooth in-and-out linear motion of the plunger 202 along the worm gear 203. Thread friction drives the shaft, directly converting rotary motion to linear motion. These linear actuators are capable of nanometer resolution and high force output (5 Newtons) at speeds ranging from 1 μm/second to 10 mm/second. The motor operates from 2.8 to 5.5 VDC sources and draw 100 mW to 900 W when moving, depending on motor speed and load. The piezoelectric motor 205 will hold its last position within the reservoir 201 when completely powered down. The advantage of using a squiggle motor as the piezoelectric motor 205 is that it generates no magnetic fields and can be made from non-ferrous metals to ensure MRI compatibility. The osteogenetic agent or agents 103 expelled from the output port 206 of the reservoir 201 travels through the catheter 207 and to the inlet port 104 of the interbody spinal cage 100.

Figure 4:
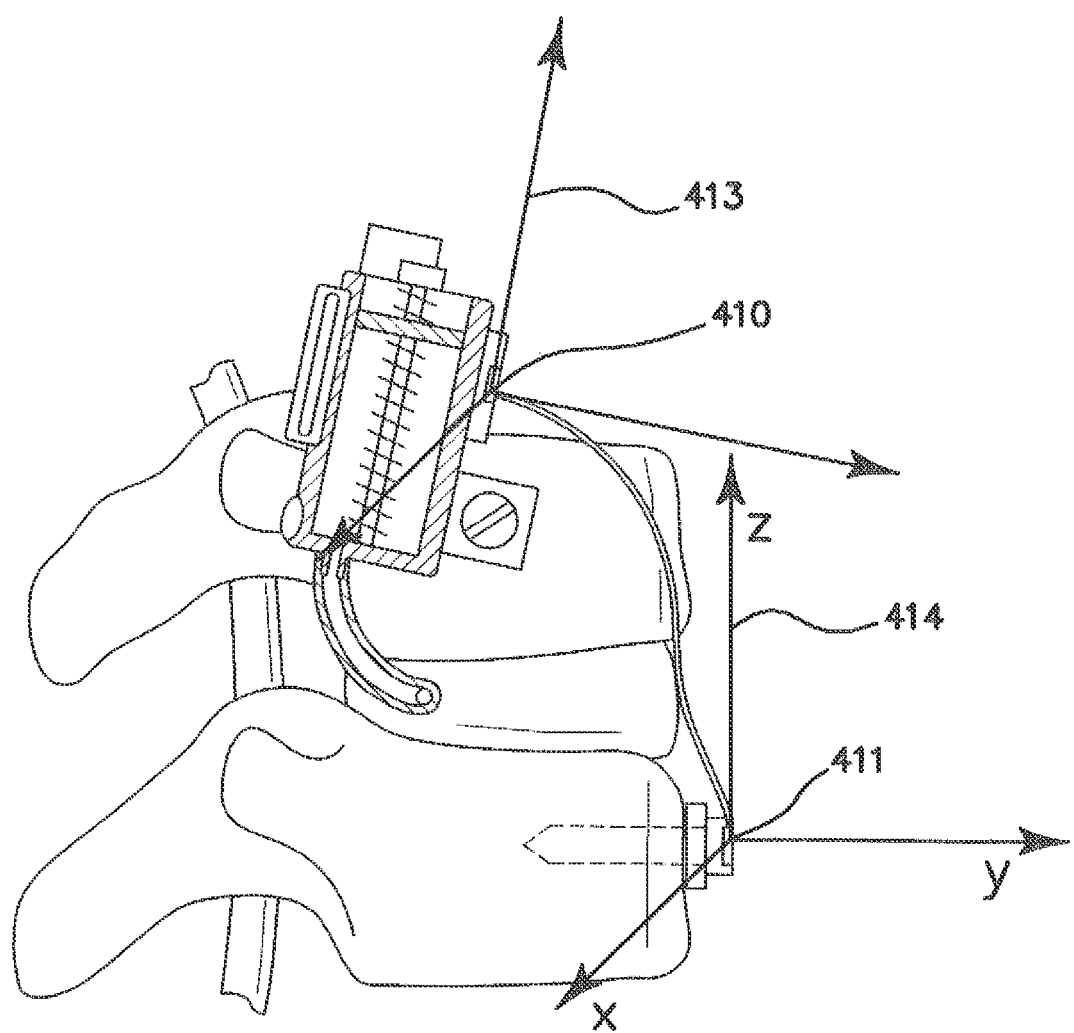
FIG. 4 is a magnified side plan view of the spinal pump assembly with accelerometers coupled to the spinal pump.

In another embodiment, a plurality of accelerometers 410, 411 may be coupled to the system as seen in FIG. 4. The spine pump accelerometer 410 is coupled directly to the spine pump 200 while the vertebra accelerometer 411 is electronically coupled to the spine pump 200 by means know in the art and physically coupled to the vertebra 11 located beneath the spinal cage 100 by means known in the art. Each accelerometer 410, 411 comprises a corresponding reference axis 413, 414 so as to enable monitoring of the progress of the bone fusion by monitoring the difference in motion of the two adjacent bone vertebrae 11 that the interbody spinal cage 100 is coupled to. It is important to note that because the reference axes 413, 414 may not be perfectly aligned, simple comparison between individual axes may not be sufficient.

Figure 5A:
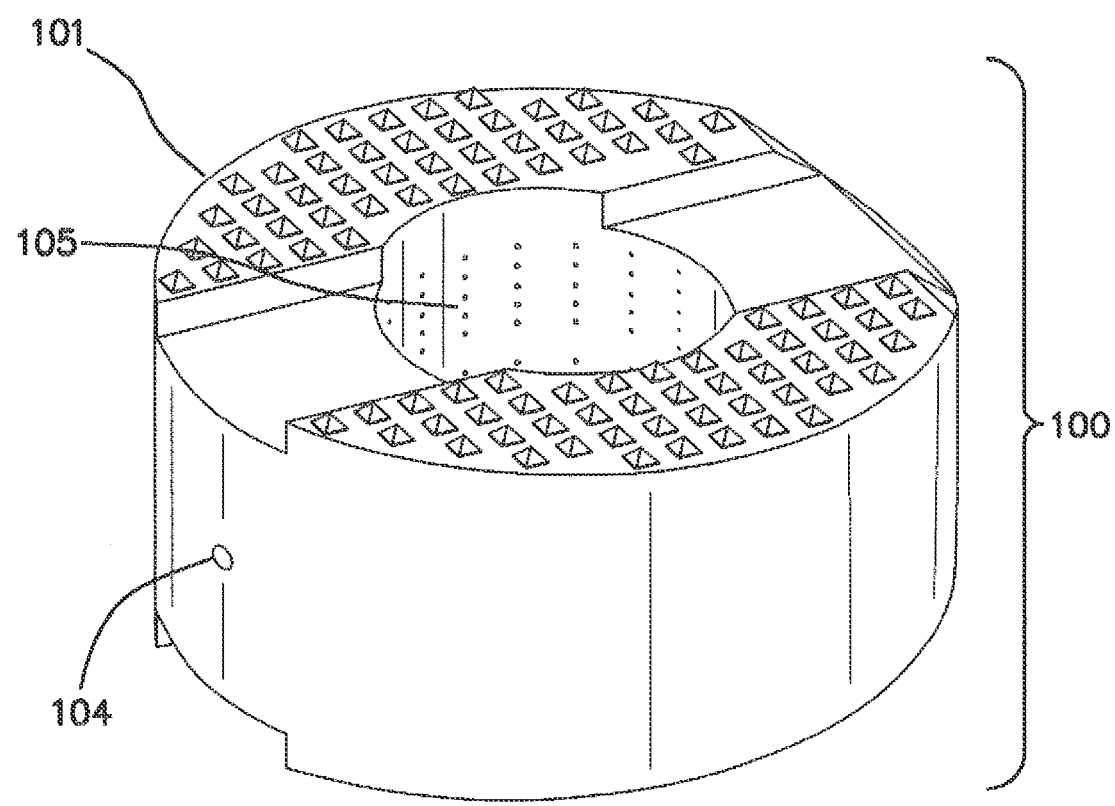
FIG. 5a is a magnified isometric view of the interbody spinal cage assembly showing the inlet port as well as the outlet pores.
Figure 5C:
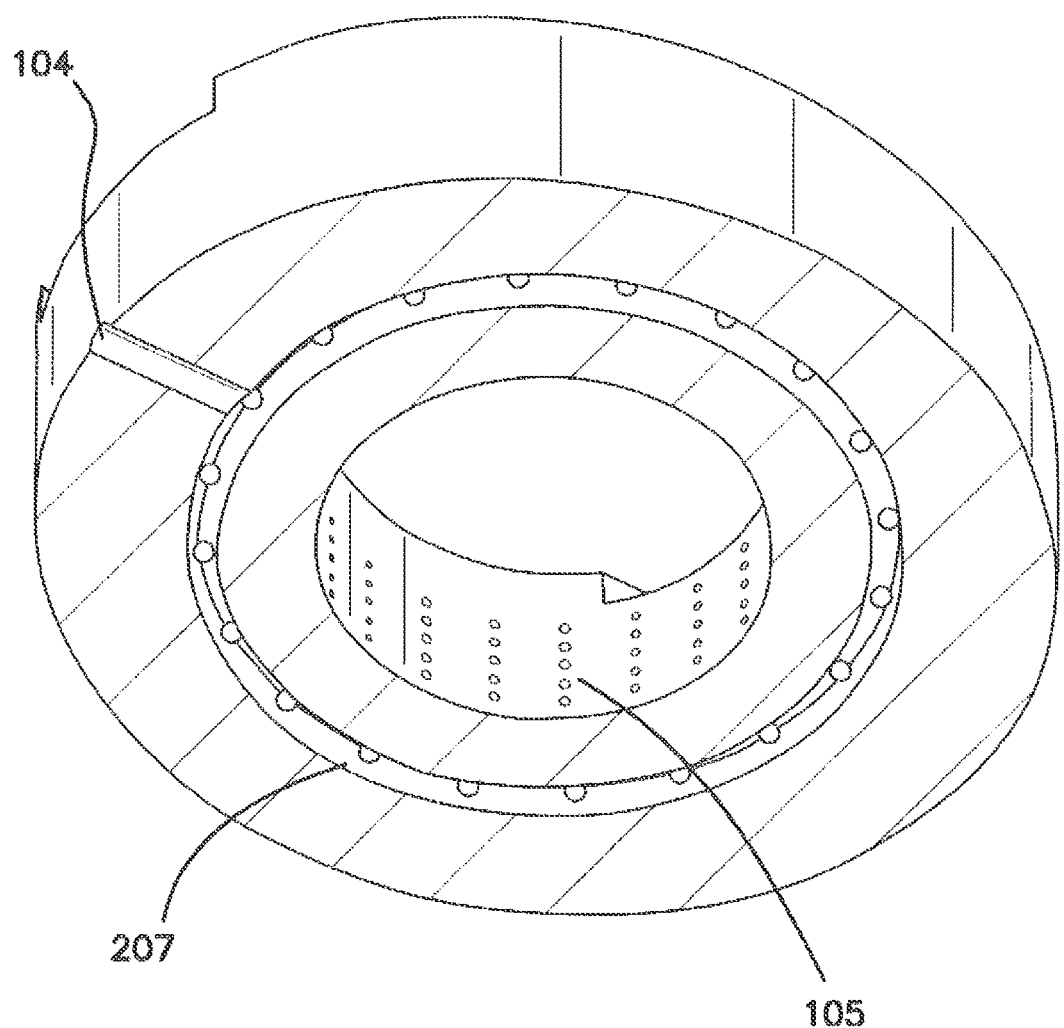
FIG. 5c is an isometric horizontal cross section of the interbody spinal cage showing the main internal channel which connects the inlet port to the outlet pores.
Figure 5D:
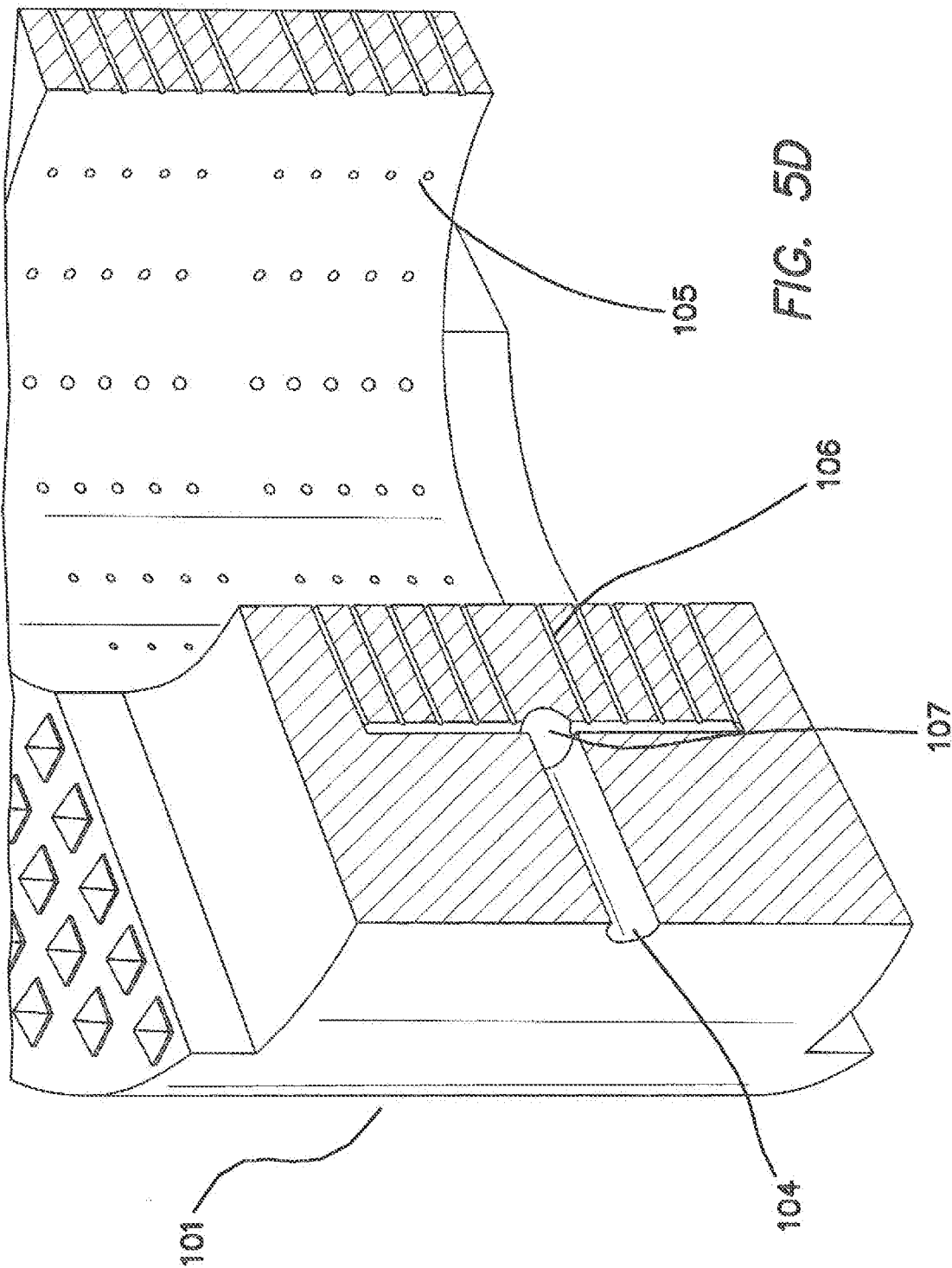
FIG. 5d is a magnified isometric vertical cross sectional view showing the outlet pores of the interbody spinal cage.

FIGS. 5a-5d are isometric depictions of the interbody spinal cage 100. The interbody spinal cage 100 comprises a cage body 101 that acts as a plumbing system to distribute the osteogenetic agent 103 that enters the inlet port 104 and into a main internal channel 107 as best seen in FIGS. 5b-5d. From the main internal channel 107, the osteogenetic agent 103 is diverted into a network of internal flow sub-channels 106 and finally out of the cage body 101 through a plurality of outlet pores 105 into an absorbable collagen sponge 102 that resides within an inner cavity of the spinal cage 100 as seen in FIG. 3a. The internal flow sub-channels 106 and outlet pores 105 allow for the osteogenetic fluid 103 to be evenly distributed throughout the collagen sponge 102 ensuring even and consistent bone formation in and around the interbody spinal cage 100.

Returning to FIG. 5b, an isometric vertical cross section of the interbody spinal cage 100 is shown which displays the main internal channel 107 and internal system of sub-channels 106 which link the inlet port 104 to the plurality of outlet pores 105. Here it can be seen that the network of internal sub-channels 106 are disposed both above and below the main internal channel 107. FIG. 5c is an isometric horizontal cross section of the interbody spinal cage 100 which shows the main internal channel 107 as defined circumferentially around an inner radius of the internal spinal cage 100 and links the inlet port 104 to the network of internal sub-channels 106 and then to the outlet pores 105. FIG. 5d is a magnified perspective cross sectional view of the external surface of the cage body 101 and the outlet pores 105. It is to be expressly understood however that the specific configuration of the main internal channel 107 and the network of internal sub-channels 106 shown in FIGS. 5a-5d, namely the main internal channel 107 being defined circumferentially about an inner radius with five periodic sub-channels 106 extending above and five periodic sub-channels 106 extending below, is for illustrative purposes only. Any configuration that uniformly and evenly distributes an osteogenetic agent about an absorbable sponge using a main channel with smaller sub-channels extending therefrom may be used without departing from the original spirit and scope of the invention.

Figure 6:
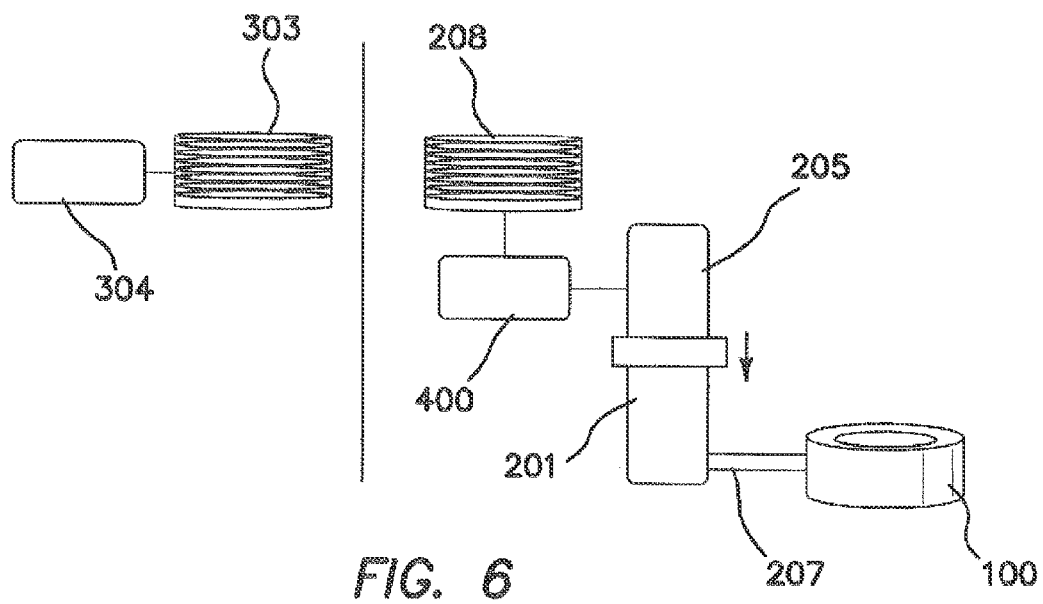
FIG. 6 is a block diagram demonstrating how power that is received from an inductive charger activates a piezoelectric motor that drives a plunger that pushes medicating agent out of a reservoir contained within the spinal pump.

FIG. 6 is a functional block diagram of the current system showing how the power received from the inductive charger and control unit 301 which comprises a belt electronic control system 304 coupled to a set of belt charger coils 303. The inductive charger and control unit 301 activates the piezoelectric motor 205 by means of a set pump induction coils 208 coupled to pump electrical control system 400. Once properly energized, the piezoelectric motor 205 in turn drives the plunger 202 to push the osteogenetic agent 103 out of the reservoir 201, through the catheter 207, and into the interbody spinal cage 100.

Figure 7:
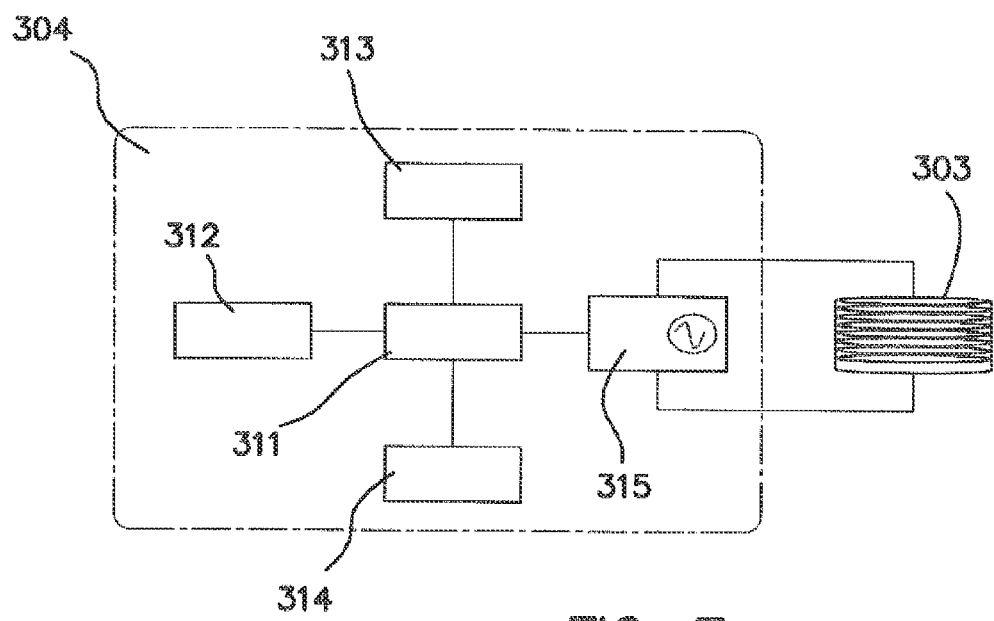
FIG. 7 is a schematic diagram representing the inductive charger in a belt.

FIG. 7 is a schematic representation of the electronic control system 304 portion of the inductive charger and control unit 301 in the belt 300. The electronic control system 304 comprises an inductive voltage generator circuit 315 on a printed circuit board and inductive belt charger coils 303 for wireless recharging. The electrical control system 304 further comprises a microcontroller 311 that manages a short-range wireless communication chip 312 and a display 313 as is known in the art. The microcontroller 311 receives a set of dosing instructions from a clinician via the wireless communication chip 312. The microcontroller 311 then relays those instructions on to the induction voltage generator 315. It is in this fashion that the dosing schedule or duration relayed to the spine pump 200 may be altered or changed mid treatment of the patient. The wireless communication chip 312 may be any wireless receiving/transmitting device, such as a Bluetooth® chip or other similar device. The display 313 may be any visual screen known in the art such as a computer monitor or the like. The entire belt electrical control system 304 is powered by a battery 314, which may be recharged from a wall socket standard in the art.

FIG. 8 is an orthographic representation of the belt 300 comprising of the inductive charger and control unit 301 coupled to a strap 305. The inductive charger and control unit 301 is enclosed in the back of the strap 305 facing the spine pump 200 implanted in the lumbar section of the human spine 10. When charging of the spine pump 200 is required, the patient wraps the strap 305 of the belt 300 around their waist with the inductive charger and control unit 301 substantially over the area where the spinal pump 200 is implanted. The patient then couples to the two opposing ends of the strap 305 together by means of a buckle or by other means known in the art so that the belt 300 remains in a stationary position as the spine pump 200 recharges. It is in this fashion that the patient may remain mobile while their implanted spine pump 200 is being recharged. Once recharged, the patient may decouple the opposing ends of the strap 305 and thus remove the belt 300 from around their waist. The inductive charger and control unit 301 portion of the belt 300 may then be plugged into a wall socket as is known in the art so that it may be sufficiently energized and ready for when the spine pump 200 is once again depleted.

Figure 9:
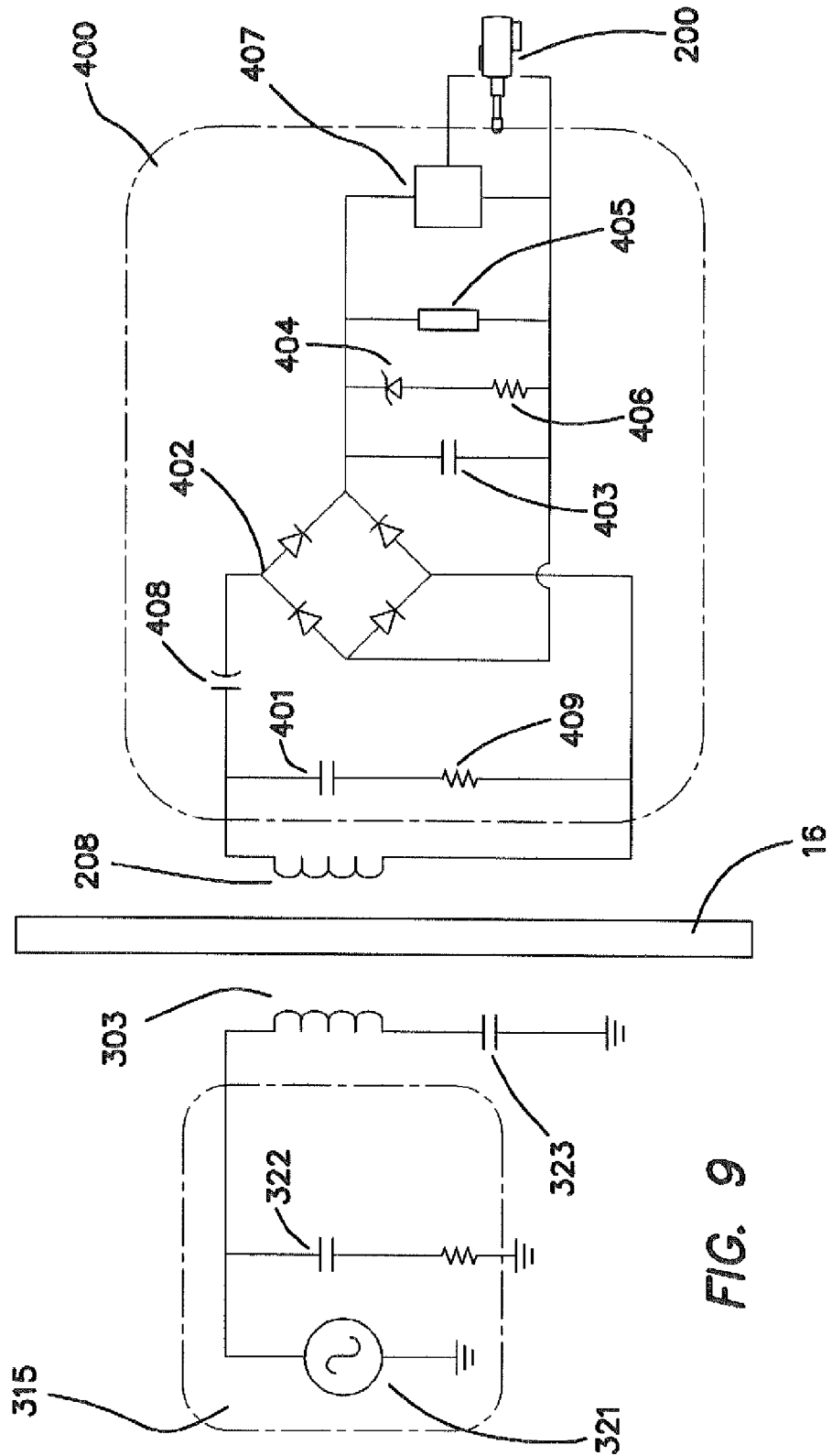
FIG. 9 is a schematic circuit diagram of the electronic circuits contained within the spinal pump, including the inductive coupling of the charger.

FIG. 9 is a schematic diagram of the induction voltage generator circuit 315 and the pump electrical control system 400. The power to the pump electrical control system 400 on the right is provided by the induction voltage generator circuit 315 on the left using inductive coupling through a portion of human skin 16. The power is transmitted inductively at 200 kHz, which is rectified by a diode bridge 402 in the pump electrical control unit 400 for use by a piezoelectric pump driver circuit 407 to drive the spine pump 200.

Figure 10:
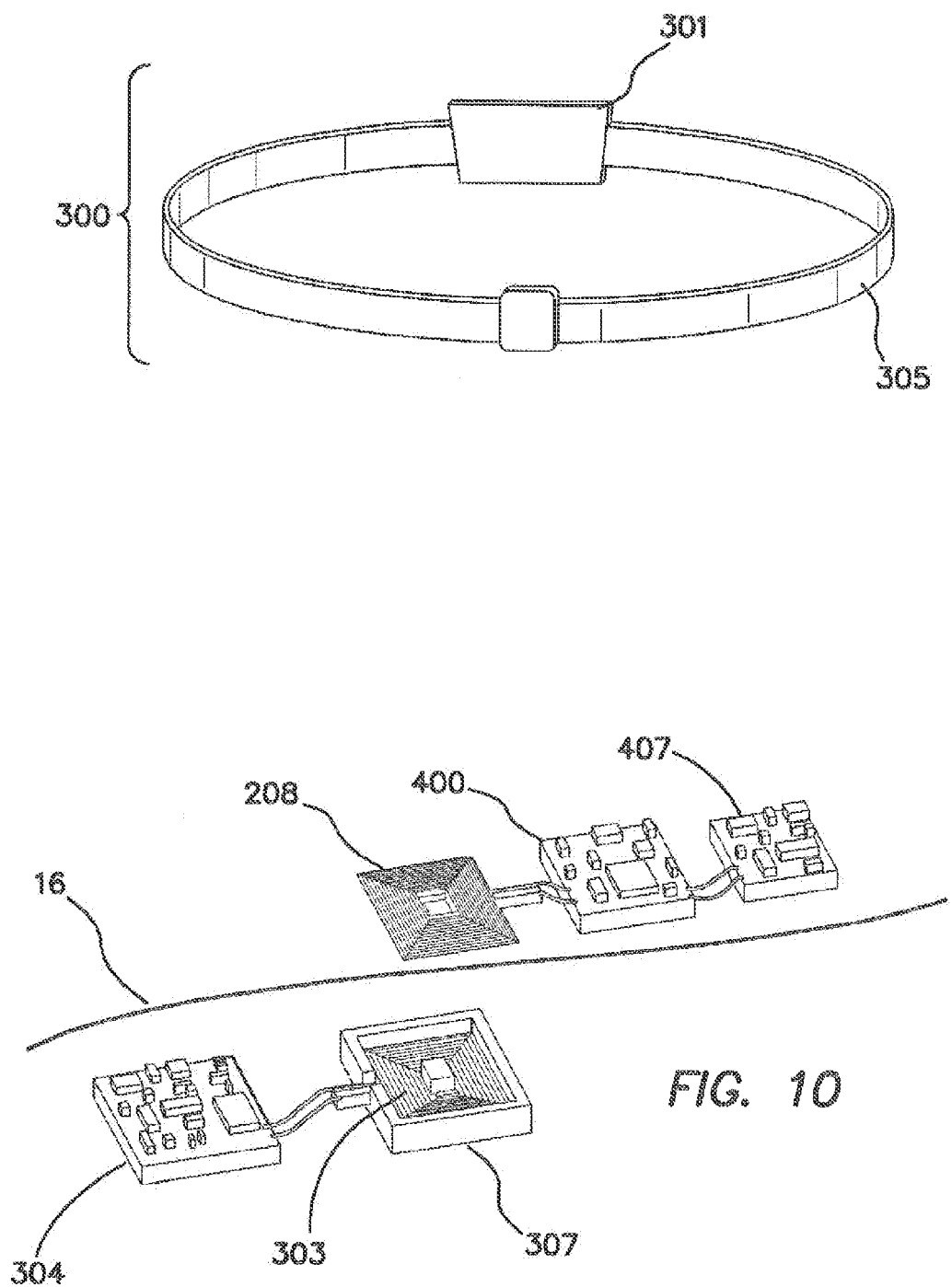
FIG. 10 is an orthographic view of the electronic circuits contained within the spinal pump, including the inductive coupling of the charger.

FIG. 10 is a three dimensional representation of the components depicted in FIG. 9, including both the internal implantable components as well as the external components for wireless control and recharging through the portion of human skin 16. The induction voltage generator circuit 315 generates alternating current by means of an alternating current source 321 that energizes the belt charger coils 303 inside of a ferrite enclosure 307. The pump electrical control system 400 receives the generated power and control signals from the pump inductive coils 208 and drives the piezoelectric driver circuit 407.

In one embodiment of the current device, the piezoelectric driver circuit 407 employs a diffusion model algorithm acting as a traffic manager governing the spine pump 200 and/or piezoelectric motor 205. The diffusion model permits a systematic and targeted osteogenetic agent 103 delivery into the spinal region 10 by predicting achievable volumes of distribution for therapeutic agents based on the established transport and chemical kinetics models. The model can be simulated in a computer-aided analysis before the actual placement procedure, thus reducing the need for trial-and-error animal experimentation or intuitive dosing in human trials. The diffusion model is used to describe the drug dispersion in the spinal disc 12 space due to both diffusion and convection. Specifically, spine geometry, drug properties, catheter dimensions and placement, and injection method are considered in this model. Other terms such as drug decomposition, chemical kinetic reaction, and bio-elimination can be incorporated to improve the accuracy of the prediction model.

The spine 10 including the ACS region is partitioned into small triangular and quadrilateral elements using Delaunay triangulation. Each small finite volume is linked to its neighbors so as to form a logically connected computational mesh, which can be generated by grid generation software such as Fluent 2007. The grid sizes need to be large enough to minimize the number of volume elements for calculations yet small enough to be able to spatially resolve the anatomical properties of the fusion area. The flow and mass transfer equations are enforced over the computational domain consisting of these meshes.

The drug delivery to the spine 10 is simply modeled as inserting aqueous solution consisting of drug solutes into the porous ACS via an infusion catheter. The aqueous solution is assumed to be an incompressible Newtonian fluid whose motion can be described by the mass and momentum conservation equation. Additionally, the drug distribution is described by the species transport and chemical kinetics equations. The diffusion model consists of two parts: the flow inside the catheter and the flow in the ACS.

For the flow inside the catheter 207, the model divides the space inside the lumen of the catheter 207 into small finite elements. The fluid flow between the finite elements is modeled with the continuity and Navier-Stokes equations as shown in Equations 1 and 2, respectively. The continuity equation (Eq 1) describes that the fluid is incompressible.

$$\vec{\nabla} \cdot (\rho \vec{v}_f) = 0 \qquad (1)$$

The Navier-Stokes equation (Eq 2) describes that the momentum of the fluid flow is conserved. It states that any change in fluid velocity in the catheter 207 (the left-hand side of the equation) is due to the pressure gradient (caused by the spine pump 200) and resistance of the flow due to fluid viscosity.

$$\rho \left( \frac{\partial \vec{v}_f}{\partial t} + \vec{v}_f \cdot \vec{\nabla} \vec{v}_f \right) = -\vec{\nabla} p + \mu \vec{\nabla}^2 \vec{v}_f \qquad (2)$$

The movement of the drug molecules inside the catheter 207 due to the flow can be modeled with the species transport equation as shown in Equation 3. It states that the change in concentration of the molecules due to diffusion and convection (the left-hand side of the equation) depends on the divergent of the product of the diffusivity and concentration gradient of the molecules in the fluid.

$$\frac{\partial C_f}{\partial t} + \vec{v}_f \cdot \vec{\nabla} C_f = \vec{\nabla} \cdot (D_b \vec{\nabla} C_f) \qquad (3)$$

The flow inside the ACS is modeled as the fluid flow in a porous medium. The ACS is partitioned into small finite elements and the flow between these elements is modeled with the continuity equation and Darcy's Law as shown in Equations 4 and 5, respectively. The continuity equation (Eq 4) describes that the loss of fluid in the flow is due to the absorption into the porous medium. The fluid velocity in tissue is related to average fluid velocity through porous tissue, $\vec{v} = \varepsilon \vec{v}_p$, through the porosity. At the tip of the catheter 207, the average fluid velocity is the same as the fluid velocity coming out of the catheter 207: $\vec{v}_p = \vec{v}_f$. The amount of fluid loss captured in the sink term is a function of the difference between the spinal fluid pressure and the venous pressure: $S_B = f(p - p_v)$.

$$\vec{\nabla} \cdot (\rho \vec{v}_t) = S_B \qquad (4)$$

The fluid dynamics in the porous ACS is embodied in Darcy's Law (Eq 5), which states that the momentum of the fluid flow is conserved. It states that any change in fluid velocity in the ACS (the left-hand side of the equation) is due to the pressure gradient (caused by the flow out of the catheter 207) and resistance of the medium to the flow.

$$\frac{\rho}{\varepsilon} \left( \frac{\partial \vec{v}_t}{\partial t} + \varepsilon^{-1} (\vec{v}_i \cdot \vec{\nabla}) \vec{v}_i \right) = -\vec{\nabla} p - R^{-1} \vec{v}_t \qquad (5)$$

The movement of the drug molecules inside the ACS due to the flow described in Eq 5 can be modeled with the species transport equation as shown in Equation 6. It states that the change in concentration of the molecules due to diffusion and convection (the left-hand side of the equation) depends on the divergent of the product of the diffusivity tensor of the ACS medium and concentration gradient of the molecules in the fluid. The accuracy of the model can be improved by incorporating the loss of drug molecules due to decomposition and bio-elimination.

$$\varepsilon \frac{\partial C_t}{\partial t} + \vec{v}_i \cdot \vec{\nabla} C_t = \vec{\nabla} \cdot (D_o \vec{\nabla} C_t) + R(C_t, \vec{x}) + S(C_t, \vec{x}) \qquad (6)$$

The completeness of the diffusion model is captured in the boundary condition assumptions listed below. At the inlet of the catheter 207, the infusion flow rate or pressure and concentration of drug are assumed to be constant. At the interior wall inside the lumen of the catheter 207, the flow is assumed no slip, $$\frac{\partial p}{\partial n} = 0,$$

and the drug doesn't penetrate (zero flux) into the catheter 207 wall, $\vec{n} \cdot \vec{\nabla} C_f = 0$ and $\vec{v}_f = 0$. At the outer surface of the catheter 207, the same boundary conditions are assumed as in the inside. At the tip of the catheter 207, the continuity of flow is assumed: $\vec{v}_f|_{lumen} = \vec{v}_{Cont} = \vec{v}_t$, and, $p_{lumen} = p_{Cont}$, $C_f|_{lumen} = C_t$. Molecule transfer through permeable boundary is only one way; drug molecules can leave but cannot return. Bio-elimination "sink term" is assumed as a function of the difference between interstitial pressure and venous pressure: $S_B = f(p - p_v)$.

The six partial differential equations (Eq 1-6) are applied to the discrete volumes in the model to produce a set of non-linear algebraic equations for the entire system. These equations are solved with proper boundary condition using the iterative Newton-Krylov method and simulated using commercial fluid dynamics software such as Fluent.

In another embodiment, the power for the piezoelectric motor 205 is provided by the transcutaneous power transmission via an inductive non-contact link. The inductive link consists of two resonance magnetic circuits, namely the induction voltage generator circuit 315 assembled externally on a belt, and the pump electronic control system 400 as part of the implanted system. The inductivities of the two resonant magnetic circuits are realized by two coils, pump induction coils 208 and belt charger coils 303. The two coils 208, 303 when facing each other form a transformer which allows energy transfer from the induction voltage generator circuit 315 to the pump electronic control system 400. Inductive links have been investigated with regard to optimization of efficiency of power transfer and the tolerance to coupling coil misalignment. All these links are designed to operate at a fixed frequency at 200 kHz.

The transfer resonant circuit is series-tuned with a voltage source with two transistors switching the rails of power supply in the electrical control system 304 in the belt 300. An oscillator generates the 200 kHz transmission frequency. Equation 7 describes the resonant equation used to derive the required number of turns in the coils.

$$f_p = \frac{1}{2\pi\sqrt{L_p C_r}} \tag{7}$$

Given the frequency at 200 kHz and a capacitor at 0.47 uF, the number of turns required for the belt charger coils 303 is calculated to be 18 turns. The voltage gain for the transformer circuit is shown in Equation 8, where the turn ratio n=Np/Ns. Given Vin=24 V and Vo=8 Vpp, the number of turns required for the pump induction coils 208 is approximately 45 turns.

$$M = \frac{2n \cdot V_o}{V_{in}} \tag{8}$$

Returning to FIG. 9, the induction voltage generator circuit 315 of the inductive charger and control unit 301 comprises H-bridge power switching stages that provide a high frequency 200 kHz alternating polarity square wave voltage into a resonant LC tank comprising the belt charger coils 303 and a first belt capacitor 323. An additional RC circuit comprising of a second belt capacitor 322 and a belt resistor 321 provides high frequency EMI filtering to reduce unwanted EMI radiation from entering into the LC tank. Without the'presence of the pump electronic control system 400 the charge of the LC tank will reside above the resonant frequency of the LC tank (200 kHz) therefore negligible current will flow through the LC thank and thus only a very low intensity magnetic field will be present. Once the pump electronic control system 400 comes within approximately 2-3 inches from the induction voltage generator circuit 315, the charge of the circuit will lower to the switching frequency of the induction voltage generator circuit 315. The magnetic flux will then induce current to flow into the pump induction coils 208. Tuning of the pump electronic control system 400 is achieved with selecting the appropriate value of a first pump capacitor 408 with relation to the load provided by the diode bridge 402. The alternating current in the pump induction coils 208 is full wave rectified by the diode bridge 402. The bus voltage of the raw rectified voltage is clamped by a Zener diode 404 which has a current limit resistor 406 to set the unloaded current of the resonant circuit. A second pump capacitor 403 provides filtering to reduce the remaining 400 kHz ripple voltage appearing after the diode bridge 402. A third pump capacitor 405 and an RC circuit comprising a fourth pump capacitor 401 and a pump resistor 409 provide EMI filtering. The piezoelectric pump driver circuit 407 steps the raw bus voltage down to a stable 5V direct current capable of powering the plunger 202 of the spine pump 200.

In another embodiment, the sensory apparatus noted by the invention provides input data so as to form a homeostatic loop, hence a regulated process using boundary conditions can attenuated and be adaptable to stimuli from local sensory data set.

In one embodiment, the current system comprising the two accelerometer sensors 410, 411 are used to monitor the progress of fusion between the two spinal bone segments. When the two bone segments are totally fused, the difference in acceleration of the two vertebras 11 above and below the spinal cage 100 should be within a tolerance factor as shown in Equation 9.

$$\vec{a}_A - \vec{a}_B < \vec{\epsilon} \tag{9}$$

However, the accelerometer sensors 410, 411 detect the sum of the acceleration of the bone segment and the acceleration due to gravity. As a result, the acceleration due to gravity must be subtracted dynamically from the sensor output as shown in Equation 10.

$$\vec{a}_A = \vec{s}_A - \vec{g} \tag{10}$$

The two accelerometer 410, 411 sensor outputs are calibrated when stationary, i.e. the outputs of the two accelerometers 410, 411 are the same, for a period of time.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A method for osteogenetic treatment in a patient comprising:
   surgically implanting a selectively controllable and inductively rechargeable spine pump with a wireless transceiver and with a fluid reservoir for holding an osteogenetic agent into a patient, the spine pump including a first accelerometer fixed thereto;
   fixing the spine pump to a selected vertebra of the patient, where the selected vertebra is to be fused to an adjacent vertebra;
   surgically implanting a spinal cage having a fluid distribution subsystem defined therein into a vertebra disc space between the selected vertebra and an adjacent vertebra, which is to be fused to the selected vertebra;
   fluidicly communicating the spine pump to the fluid distribution subsystem of the spinal cage;
   surgically implanting a fitting fixed to the adjacent vertebra;
   coupling a second accelerometer to the fitting fixed to the adjacent vertebra;
   electrically communicating the first and second accelerometers to the wireless transceiver in the spine pump;
   selectively dispensing selected amounts of osteogenetic agent from the fluid reservoir to the fluid distribution subsystem in the spinal cage over an extended time period of treatment during which the selected and adjacent vertebrae are fusing together, the amount of osteogenetic agent delivered to the fluid distribution subsystem in the spinal cage being alterable during the extended time period of treatment according to a set of received dosing instructions wirelessly transmitted to the receiver of the spine pump over a communications link exterior to the patient;
   calibrating the first and second accelerometers by means of the wireless transceiver when the patient and consequently the selected and adjacent vertebrae are stationary in space to remove the effect of gravity upon the calibration of the first and second accelerometers;
   monitoring the first and second accelerometers by means of the wireless transceiver while the patient is ambulatory;
   determining the vector difference in the outputs of the first and second accelerometers to assess the efficacy of osteogenetic treatment of the vertebra disc space between the selected and adjacent vertebrae; and
   selectively modifying amounts of the osteogenetic agent to be dispensed from the fluid reservoir to the fluid distribution subsystem in the spinal cage over an extended time period of treatment in response to the assessed efficacy of osteogenetic treatment of the vertebra disc space between the selected and adjacent vertebrae as determined by the vector difference in the outputs of the first and second accelerometers.

2. The method of claim 1 further comprising inductively recharging the spine pump by:
   placing an external inductive charger substantially over the area where the spine pump has been implanted;
   generating an induced voltage in the inductive charger;
   driving the induced voltage through a plurality of induction coils in the induction charger;
   receiving the induced voltage through a plurality of induction coils in the spine pump; and
   driving a piezoelectric motor within the spine pump with the received induced voltage.

3. The method of claim 1 where selectively dispensing the osteogenetic agent from the reservoir of the spine pump to the spinal cage comprises:
   driving a piezoelectric motor with an induced voltage;
   pushing down a plunger within a reservoir in the spinal pump; and
   dispensing the osteogenetic agent out of a outlet port defined within the reservoir.

4. The method of claim 1 where selectively dispensing comprises:
   introducing the osteogenetic agent into a main internal channel circumferentially defined within an inner radius of the spinal cage;
   diverting the osteogenetic agent into a network of sub-channels coupled to the main internal channel and disposed about the spinal cage; and
   distributing the osteogenetic agent evenly about an absorbable sponge disposed within the spinal cage by means of the network of sub-channels.

5. The method of claim 4 further comprising delivering the osteogenetic agent systematically and evenly throughout the spinal cage according to a diffusion model stored within a pump control system in the spinal pump.

6. The method of claim 1 further comprising refilling the reservoir within the spine pump with the osteogenetic agent by means of a syringe.

* * * * *